United States Patent [19]

Bierre et al.

[11] Patent Number: 5,739,000
[45] Date of Patent: Apr. 14, 1998

[54] ALGORITHMIC ENGINE FOR AUTOMATED N-DIMENSIONAL SUBSET ANALYSIS

[75] Inventors: Pierre Bierre, Redwood City; Daniel E. Thiel, Pleasanton, both of Calif.

[73] Assignee: Becton Dickinson and Company, Franklin Lakes

[21] Appl. No.: 227,155

[22] Filed: Apr. 13, 1994

Related U.S. Application Data

[63] Continuation-in-part of Ser. No. 39,465, Apr. 26, 1993, which is a continuation-in-part of Ser. No. 751,020, Aug. 28, 1991, abandoned.

[51] Int. Cl.$^6$ .................................................... G01N 33/49
[52] U.S. Cl. .................. 435/7.24; 435/2; 436/536; 436/172; 436/800; 436/805; 364/413.08; 364/571.02
[58] Field of Search .............................. 435/7.24, 968, 435/2; 436/536, 172, 800, 805; 364/413.07, 413.08, 571.01, 571.02

[56] References Cited

U.S. PATENT DOCUMENTS 4,661,913  4/1987  Wu et al. ............................. 364/500

OTHER PUBLICATIONS

Bezdek, James C. and Chiou, Er-Woon—"Core Zone Scatterplots: A New Approach to Feature Extraction for Visual Displays"; Computer Vision, Graphics, and Image Processing 41, 186–209 (1988).

*Primary Examiner*—Paula K. Hutzell
*Assistant Examiner*—Rachel Heather Freed
*Attorney, Agent, or Firm*—Allen W. Wark

[57] ABSTRACT

This invention provides a method of multi-parameter data analysis by means of a hierarchical attractor algorithmic engine. The method employs analyzing the data by construction of a population hierarchy, wherein the populations are not mutually exclusive, thereby providing an important analytical tool. The use of the hierarchical attractor algorithmic engine presents the user with far greater flexibility in such analysis, as overlapping populations can be separately examined.

13 Claims, 6 Drawing Sheets

ALGORITHMIC ENGINE FOR AUTOMATED N-DIMENSIONAL SUBSET ANALYSIS

This application is a continuation-in-part of U.S. patent application Ser. No. 08/039,465, filed Apr. 26, 1993 (pending), which in turn, is a continuation-in-part of U.S. patent application Ser. No. 07/751,020, flied Aug. 28, 1991 (abandoned).

BACKGROUND OF INVENTION

This invention addresses the need to assign classifications to multi-parameter events as they are arriving from an array of sensors. Analysis of such multi-parameter data is ordinarily accomplishing by autoclustering, i.e., forming sets of data having common characteristic(s). The convention followed by most autoclustering methods is to classify such events into a set of M mutually exclusive groupings, for example this is the approach of classical autoclustering methods such as k-Means, statistical pattern recognition classifiers, and newer schemes based on trainable neural networks and gravitational attractors.

However, the objective of analyzing into mutually exclusive groupings or populations is not easily transferable to the analysis of clinical data, as it is somewhat inconsistent with the way biologists are disposed to think about cellular populations. Such analysis is, however, one of the important applications of multi-parameter event autoclustering. Biologists tend to follow a more natural and intuitive analysis approach, placing each event somewhere in a population hierarchy, wherein populations are not necessarily mutually exclusive. This approach permits an event to simultaneously belong to separate populations drawn at differing levels of biospecificity. Thus, the events could be analyzed from a number of separate perspectives, presenting data in a form convenient and accessible to biologists and clinicians. Such analytical methods, however, have not been applied to autoclustering data analysis.

SUMMARY OF INVENTION

This invention provides a method of multi-parameter data analysis by means of a hierarchical attractor algorithmic engine. More specifically, the method employs analyzing the data by construction of a population hierarchy, wherein the populations are not mutually exclusive, thereby providing an important analytical tool.

For example, in studying the human peripheral white blood cell compartment by measuring a combination of cell surface receptor staining and passive light measurements on each cell, the scientist ordinarily begins by separating the data into mutually exclusive major subsets and then goes on to study mutually exclusive subsets within each major subset. Then one can then look at mutually exclusive subsets within those subsets, etc. At each successive level of subsetting, one is looking at fewer cells characterized by increasing biospecificity.

Figure 1:
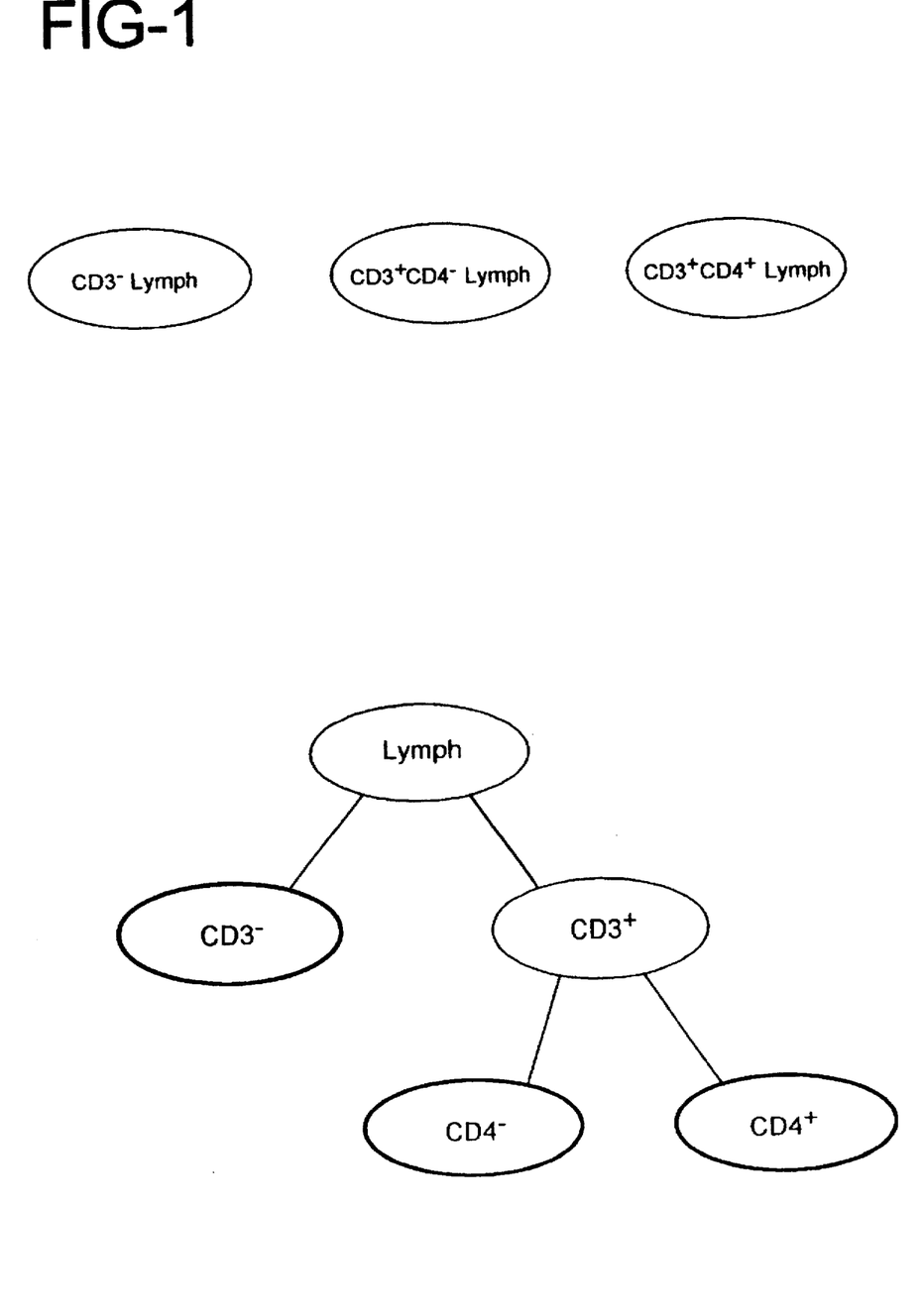
FIG. 1 presents a diagram of a mutually exclusive subset for lymphocytes into $CD3^+$ and $CD3^-$ groupings.

The scientist studying these cellular populations has traditionally been obliged to accommodate to software algorithms which only support this mutually-exclusive classification into M target groupings. For example, in subsetting lymphocytes into $CD3^+$ vs. $CD3^-$ cells, and then further subsetting the $CD3^+$ cells into $CD4^+$ vs. $CD4^-$ cells. The problem maps into the following mutually-exclusive set of target populations, each formed by conjoining its full set of constraints, as illustrated in FIG. 1.

An issue that arises for the biologist is that the second and third populations share a common characteristic, namely positive expression of CD3 antigen. At some level of abstraction where CD4 expression is ignored, they ought to be considered one undifferentiated population of $CD3^+$ cells. While it appears to be simple to merely combine the second and third populations to obtain a total $CD3^+$ count and population statistics, such software generally only computes and reports out population statistics for the 3 mutually exclusive populations; additional post-processing work must be done manually to obtain the aggregate $CD3^+$ population statistics, and then only first order statistics can be derived by post-processing. The same drawback hampers the ability to pull out a total lymphocyte population combining all 3 mutually-exclusive populations. Also, as the total number of populations increases, the complexity of this post-processing work also increases.

Figure 2:
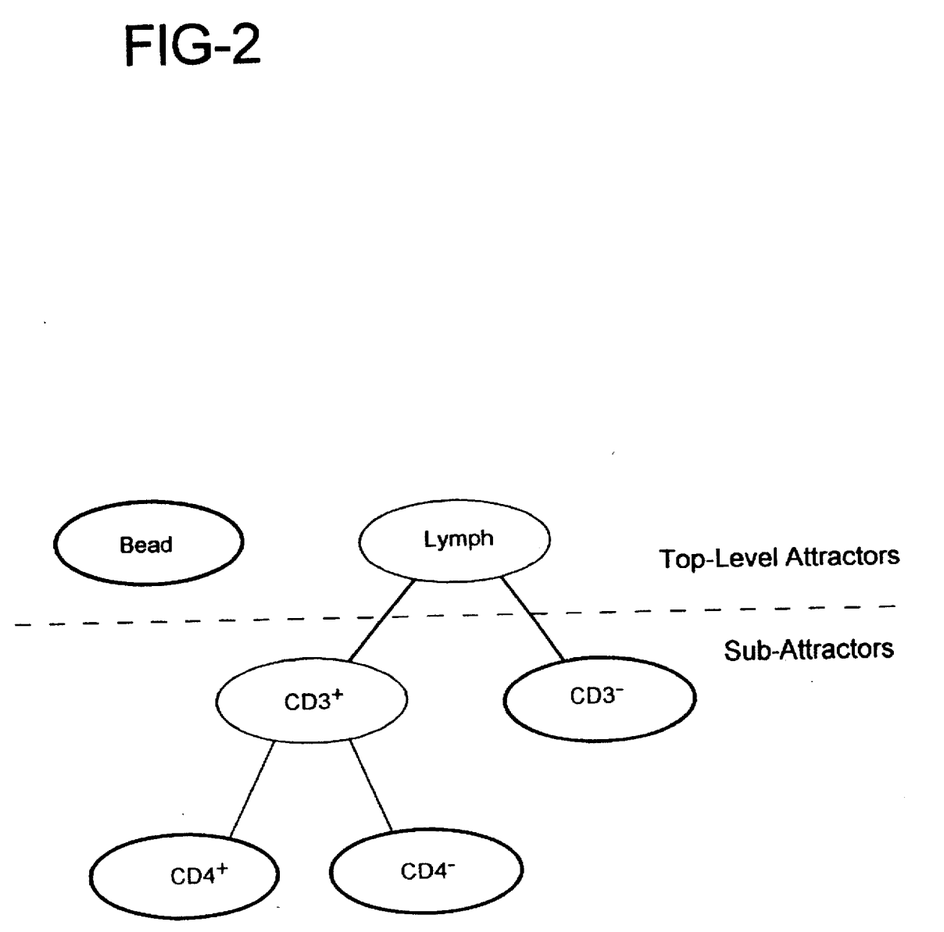
FIG. 2 presents a diagram of the same groupings using the method of this invention.

The method of the instant invention permits the scientist working on subset analysis problems to specify classification into a population hierarchy as shown in FIG. 2.

Note that the 3 terminal populations (depicted as highlighted ovals) correspond exactly to the 3 mutually exclusive populations described above. However in addition, aggregate populations are explicitly defined for $CD3^+$ and $CD3^-$ cells, and total lymphocytes.

The hierarchical attractor engine algorithm classifies each incoming event along a downward cascade of populations until it can no further be sub-classified. In the example above, a cell is first tested against the criteria for being a lymphocyte. If it qualifies, it is accumulated into the lymph population statistics, then tested to see if it can be subclassified as either $CD3^-$ or $CD3^+$. If so, the event is accumulated into the population statistics of that subset. Those cells which join the $CD3^+$ population are then tested to see if they can be subclassified as either $CD4^-$ or $CD4^+$. If so, the event is accumulated into the population statistics of that subset. Mutually exclusive classification only comes into play among sibling populations, e.g., those sharing a common parent (direct ancestor).

Separate population statistics are kept for each population of the hierarchy; thus the same event can be counted as belonging to several populations represented at different levels of the "tree". A cell counted once as a $CD3^+CD4^+$ Lymph in the "flat" (mutually-exclusive) classification system described the preceding example, will be counted 3 times in the hierarchy, by Lymph, $CD3^+$, and $CD4^+$ populations respectively.

There are several benefits that come with approaching population classification hierarchically, beyond ability to represent overlapping cell characteristics and to keep population statistics simultaneously at all levels of subset definition. These are: a) in general, the criteria for defining a subpopulation will require use of fewer parameters (lower dimensionality) when approached hierarchically because of the constraints already supplied by its "ancestor" populations, b) the scientist doesn't need to know at the outset the deepest level to which he will be subsetting, as is a requirement when devising "flat" methods, c) the percentage a population represents within its parent population (and also its grandparent population, and so on) is automatically computable, i.e. post-processing it manually from population statistics is obviated d) visualization of a single population at a time can be generalized to apply to composite as well as pure populations, and e) a population hierarchy can support, as a special case, "flat" (one-level), mutually-exclusive M-way classification in instances where such is desirable.

Taken together in combination, these benefits represent a significant advance in the art and practice of multidimensional event clustering.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

DETAILED DESCRIPTION OF INVENTION

The power of the hierarchical attractor engine algorithm owes equally to population hierarchy, and to the use of gravitation attractors [1] for defining each population's membership criterion. The algorithmic technology for, and advantages of employing gravitation attractors for computing each population's membership boundary are disclosed in the parent to patent application U.S. patent application Ser. No. 751,020, filed Aug. 28, 1991 which application is incorporated herein by reference. Such attractors get their name from the ability to move their decision surface spatially based on local interaction with data events, i.e., they incorporate a local-center-of-mass-seeking behavior into an otherwise fixed (user-seeded) geometric boundary.

This technology extends without modification to hierarchical attractors, with the trivial exception that the user must select the parent population and ask for a new sub-attractor thereof in order to define a new subset of the parent. A new attractor (as opposed to a sub-attractor) creates a new top-level population.

The algorithm underlying the hierarchical attractor classification engine represents an improvement over the previous gravitational attractor by employing a recursive Pre-analysis engine which manages the process of gravitational attraction, in place of the prior claimed "iteration-loop" Pre-analysis engine.

Also, a new recursive Classification engine manages the process of assigning events their membership into a hierarchy of populations, replacing the prior claimed iteration-loop Classification engine. A new bit-sliced classification table capable of remembering one-to-many relations between an event and populations it belongs to replaces the prior integer classification table for remembering affiliation to a single population. And, a new recursive population statistics module able to make use of the hierarchical relations among a set of attractors for calculating multi-level subset percentages replaces a prior module performing iteration loop population statistics.

The combination of prior-claimed attractor behavior with the herein-disclosed engine supporting hierarchical attractor sets (i.e. data analysis protocols specified as a hierarchy of attractors) gives rise to a host of novel, synergistic benefits. No functionality had to be traded-off in adopting a hierarchy of attractors as compared to the prior-claimed "flat" one-level attractor set classifier based on M mutually-exclusive attractors, indeed the flat attractor set is subsumed as a special-case of the more general hierarchical attractor set. Regression testing shows that equivalence of classification behavior was retained for this special case.

The significance of this inventive combination to the scientist needing to custom-build population subset analyzers that can be applied automatically and repetitively to analyze incoming datastreams or recordings of multi-parameter cellular measurements can be summarized as follows: a) the inability of M-way classifier algorithms to naturally represent overlapping properties of events (e.g. biological cells) has been overcome by allowing a classifier to be defined as a hierarchy of populations, b) the hierarchical cascading of attractors (population-defining boundaries) permits each attractor to be defined in fewer dimensions than required with flat attractor set classifiers, easing the cognitive workload of multidimensional analysis, c) a hierarchical attractor (as compared to a flat attractor) is more likely to be able to be defined in a single 2D projection of a multivariate (e.g., 5-dimensional) data distribution, making the visualization and editing of the attractor boundary facile, and d) all the extent benefits of using attractors (population drift-adaptivity, object-oriented modularity, rare-population stability) have been retained in hierarchical attractor methods of analysis automation.

For purposes of clear exposition, a relatively simple hierarchical attractor method will be described in detail. This example is chosen to convey the workings of the hierarchical attractor algorithm, but not necessarily the range of applicability of this algorithm. A multitude of applications of varying dimensionality and subset complexity, in theory can be solved by the general-purpose design of the hierarchical attractor algorithm.

Figure 3A:
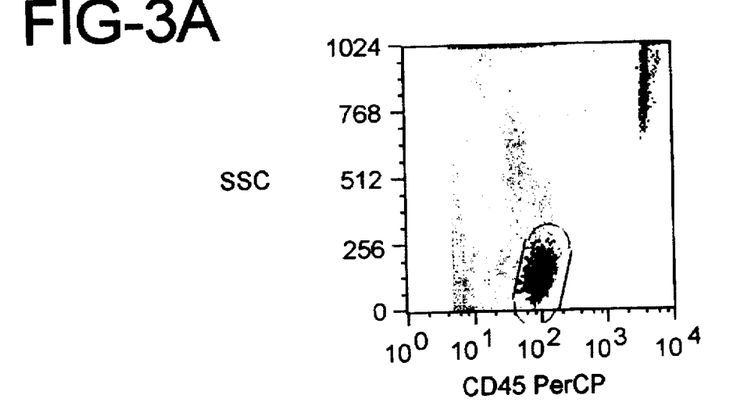
FIGS. 3A, 3B and 3C presents flow cytometric cellular recordings for a 5-dimensional data distribution wherein beads are depicted in black, Lymph cells are depicted in light blue, $CD3^+$ cells are depicted in magenta, $CD4^+$ cells are depicted in orange, $CD4^-$ cells are depicted in green, and $CD3^-$ cells are depicted in dark blue.
Figure 3B:
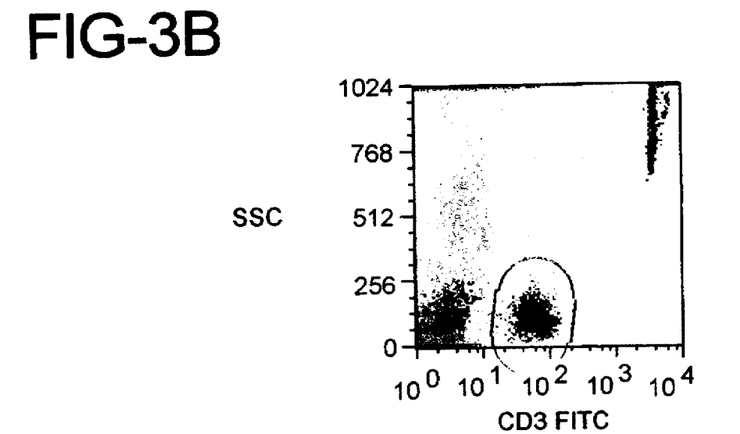
Figure 3C:
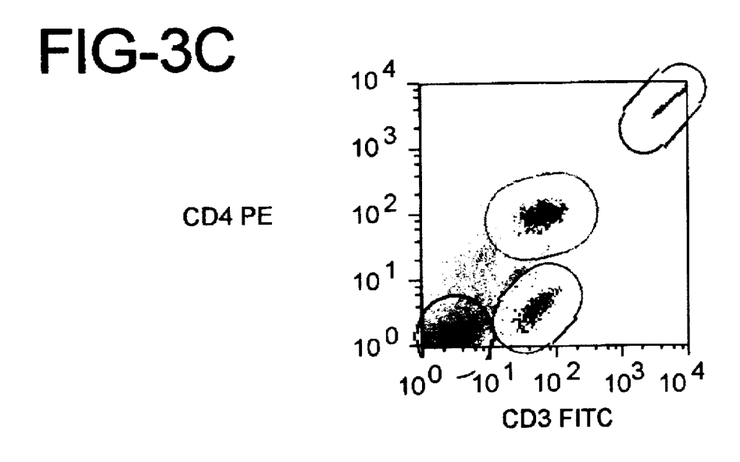

The parameter data distribution presented in FIGS. 3A, 3B and 3C is an example of a flow cytometric cellular recording analyzed using a hierarchical attractor set. The color attribute of each population is identified and cell relationships are depicted, i.e., Lymph cells with $CD3^+$ and $CD3^-$ cells, and $CD3^+$ cells with $CD4^+$ and $CD4^-$ cells. The goal of the analysis is to obtain absolute cell counts (cells/micro-liter-whole-blood) for the Lymph set and all of its subsets, and to obtain cell ratios (expressed as percentages) for each subset as a fraction of any of its "ancestor" supersets.

The purpose of the bead population is to provide a known reference concentration (beads/micro-liter-whole-blood). A nominal 50K beads is spiked into a preparation of 50 ul-whole blood, 5 ul of composite 3-color monoclonal antibody (CD3-FITC, CD4-Phycoerythrin, CD45 PerCP) let stand to incubate for 15 minutes. Then 500 ul of BD FACS Lysing Solution are added, allowing 15 min. of RBC lysing before analyzing the specimen on a FACScan Analyzer. This "lyse no-wash" preparation requires no centrifugation step for extracting WBCs.

10,000 triggered events were recorded using CD45 (HLe-1) antibody expression as the trigger signal. The 5 recorded parameters were:

Forward Light Scatter (FSC)—not used by this analysis method

Side Scatter (SSC)

CD3 FITC

CD4 PE

CD45 PerCP

The steps involved in devising the hierarchical attractor set were as follows:

1) The example data file was opened and the 3 bivariate scatterplots (CD45×SSC, CD3×SSC, and CD3×CD4) were created.

2) A new (top-level) attractor was created to classify and count the BEAD population. It was defined to operate in the 2-space [CD3×CD4], and was seeded in the upper-right corner of this 2-space, so as to visually enclose the bead cluster. This BEAD attractor was selected to serve as the absolute count reference population, and its known concentration was entered (1000 beads/ul-whole-blood).

[All attractors in this example are two-dimensional cigar-shaped attractor objects, as described in the parent to this application. Their geometry consists of a spanning 2-D "centerline" whose 2 endpoints are seeded graphically using a mouse, and a membership radius whose extent is also mouse-adjusted.]

3) A new (top-level) attractor was created to classify and count the LYMPH population. It was defined to operate in the 2-space [CD45×SSC], and was seeded in the lower-middle part of this 2-space, so as to contain the LYMPH cluster. Seeding decisions are the province of a skilled flow-cytometrist cognizant of the staining protocol and expected locations of cell populations acquired under it.

Figure 4A:
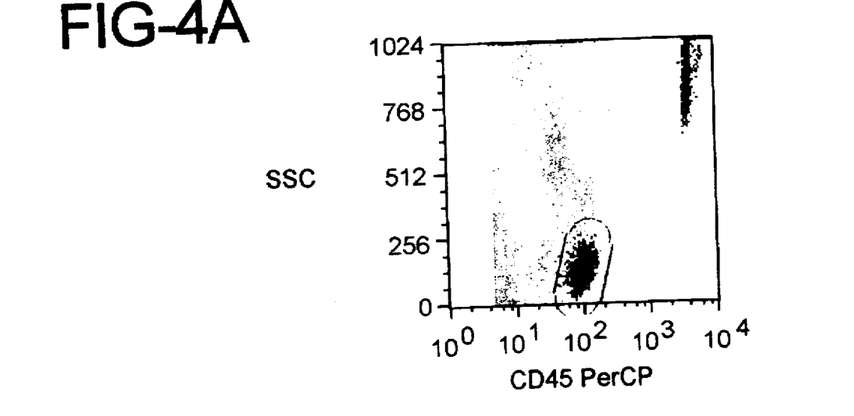
FIGS. 4A, 4B, 4C, 5A, 5B, 5C, 6A, 6B and 6C present different analyses of that of FIGS. 3A, 3B and 3C, wherein beads are depicted in black, Lymph cells are depicted in light blue, $CD3^+$ cells are depicted in magenta, $CD4^+$ cells are depicted in orange, $CD4^-$ cells are depicted in green, and $CD3^-$ cells are depicted in dark blue.
Figure 4B:
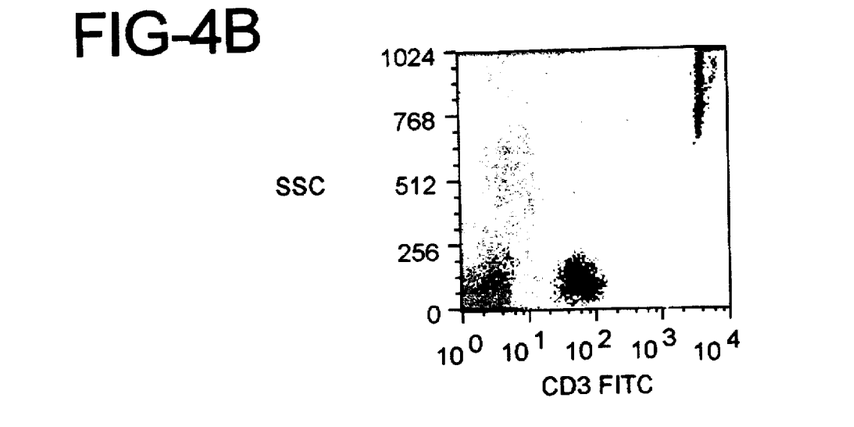
Figure 4C:
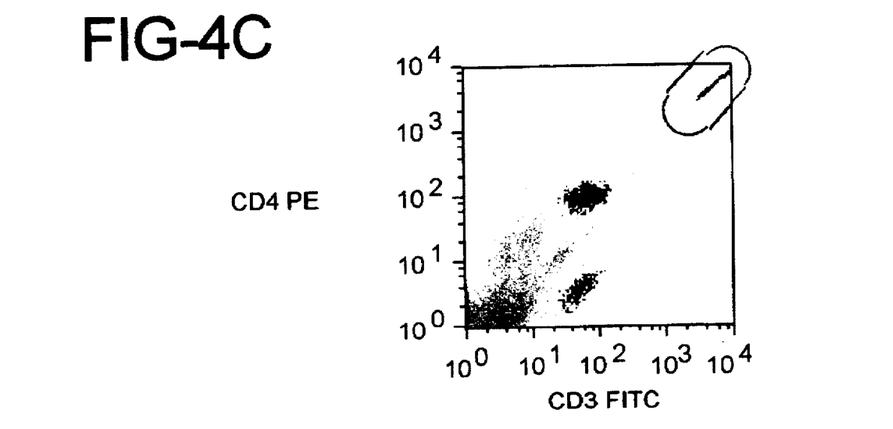

Incremental feedback was obtained by classifying the data. This process runs the hierarchical attractor algorithm, and repaints the 2D scatterplot to show the classification results, as depicted in FIGS. 4A, 4B and 4C.

Two classified populations can be seen, BEADS and LYMPHS. Up to this point, the method acts like a "flat" attractor set, i.e., a cell can be classified into one of two mutually-exclusive populations or remain unclassified (light grey dots). The next step invokes the use of a sub-attractor in order to define a subset of LYMPHS.

4) After selecting the LYMPH attractor, a new sub-attractor was created to classify and count the CD3 $^+$ subset of the LYMPH population. The sub-attractor was defined to operate in the 2-space [CD3×SSC], and was seeded in the lower-middle part of this 2-space.

5) After selecting the LYMPH attractor, a second sub-attractor was created to classify and count the CD3$^-$ subset of the LYMPH population. The sub-attractor was defined to operate in the 2-space [CD3×CD4], and was seeded in the lower-left corner of this 2-space.

Figure 5A:
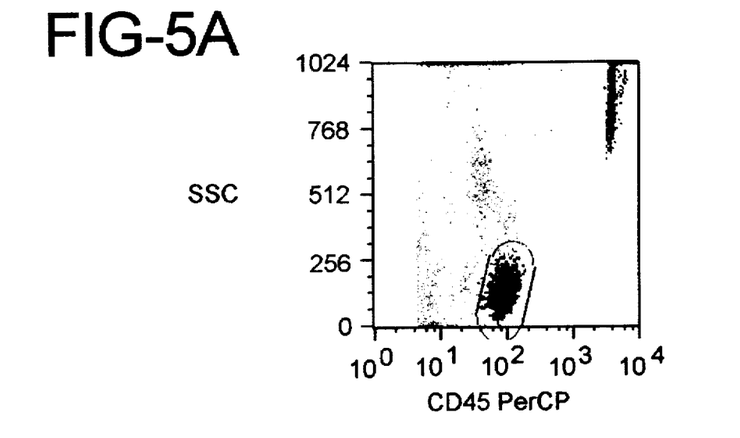
Figure 5B:
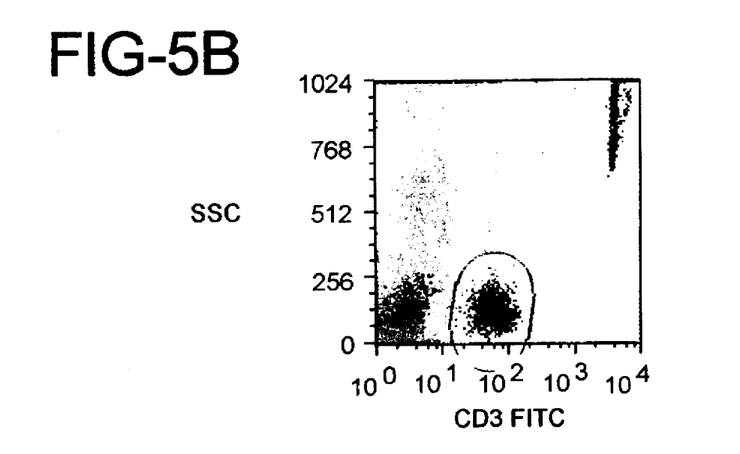
Figure 5C:
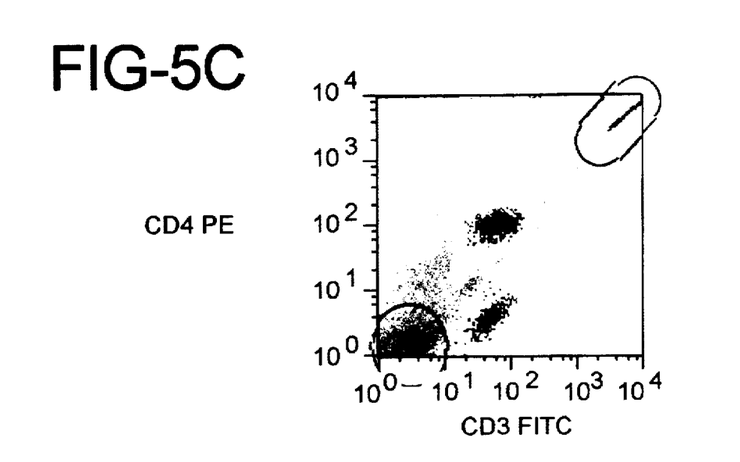

Incremental feedback was again obtained by classifying the data, as depicted in FIGS. 5A, 5B and 5C.

Note that the CD3$^+$ and CD3$^-$ subpopulations of LYMPHS are given unique color attributes. Cells that were subclassified are plotted using the subpopulation color; in general, events are plotted at the lowest level of sub-classification that is possible to plot for that event.

Next, the CD3 $^+$ population will be subsetted into its CD4 $^+$ and CD4$^-$ components.

6) After selecting the CD3 $^+$ attractor, a new sub-attractor was created to classify and count the CD4$^+$ subset of the CD3$^+$ population. The sub-attractor was defined to operate in the 2-space [CD3×CD4], and was seeded near the middle portion of this 2-space.

7) After selecting the CD4 $^+$ attractor, a "duplicate attractor" feature was used to create a sibling sub-attractor to the CD4$^+$ attractor. Its job will be to classify and count the CD4$^-$ subset of the CD3 $^+$ population. The sub-attractor was defined to operate in the 2-space [CD3×CD4], and was seeded near the lower-middle portion of this 2-space.

The hierarchical method is now complete, and is saved to file. The completed analysis is run on the data, yielding the plot presented in FIGS. 6A, 6B and 6C.

Figure 6A:
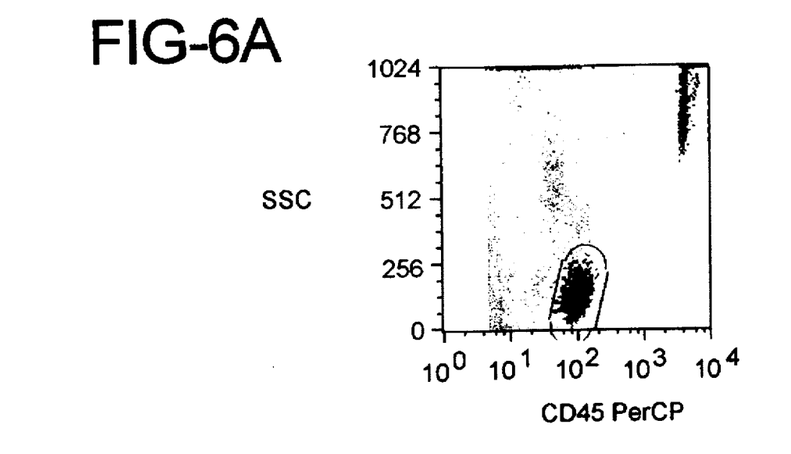
Figure 6B:
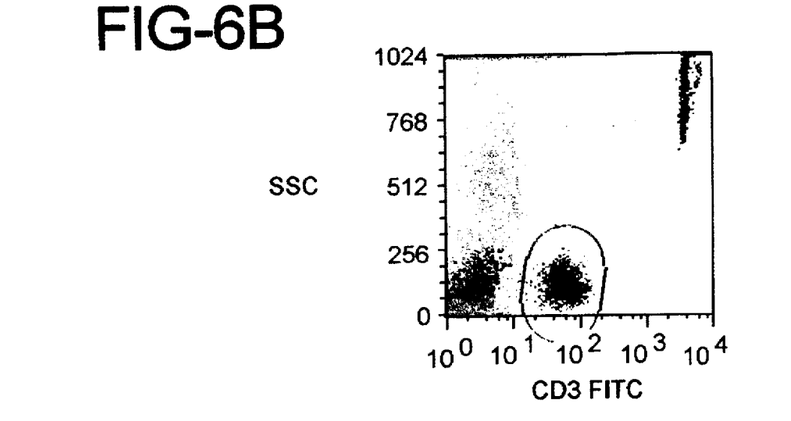
Figure 6C:
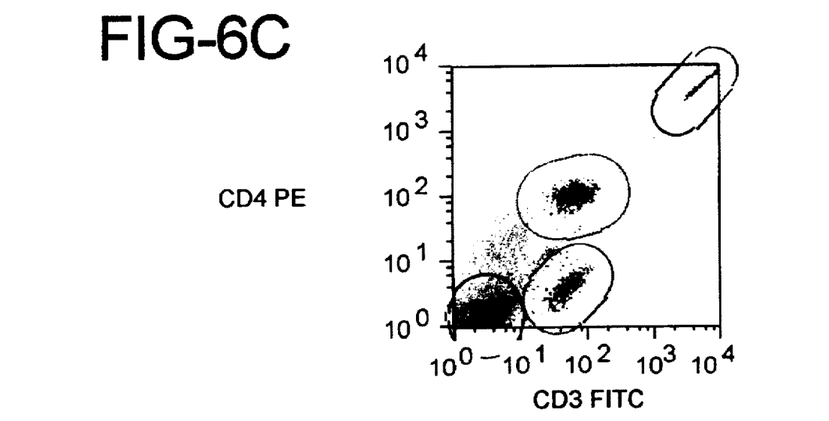

Note that the CD3$^+$ subsets pick up their own color attributes, as shown in FIG. 6.

The following population statistics report was obtained automatically at the conclusion of the classification step.

Method: CD3-4-45 Method
File: VN09013058
Sample ID: CD4/3/45 PERCP NORMAL DONOR 1
Acquired: 9/1/93

|  | Bead | | |
|---|---|---|---|
| Cluster Membership | 762 | | |
| Abs. Count | 1000.00 | | |
| Parameter | Mean | SD | CV |
| FSC__ | 78.70 | 74.74 | 94.97 |
| SSC__ | 880.10 | 106.32 | 12.08 |
| CD3 FITC__ | 931.80 | 24.72 | 2.65 |
| CD4 PE__ | 922.11 | 22.12 | 2.39 |
| CD45 PerCP__ | 934.35 | 23.44 | 2.50 |
|  | Lymph | | |
| % of Total Classified | 100.00 | | |
| Abs. Count | 2011.81 | | |
| Parameter | Mean | SD | CV |
| FSC__ | 329.19 | 87.93 | 26.71 |
| SSC__ | 130.83 | 47.48 | 36.29 |
| CD3 FITC__ | 386.69 | 139.76 | 36.14 |
| CD4 PE__ | 332.55 | 208.43 | 62.67 |
| CD45 PerCP__ | 509.57 | 25.23 | 4.95 |
|  | CD3+ | | |
| Cluster Membership | 1224 | | |
| % of Lymph__ | 79.84 | | |
| Abs. Count | 1606.29 | | |
| Parameter | Mean | SD | CV |
| FSC__ | 321.17 | 85.03 | 26.47 |
| SSC__ | 125.99 | 45.66 | 36.24 |
| CD3 FITC__ | 453.40 | 41.69 | 9.19 |
| CD4 PE__ | 405.25 | 167.02 | 41.21 |
| CD45 PerCP__ | 515.85 | 21.69 | 4.20 |
|  | CD4+ | | |
| Cluster Membership | 862 | | |
| % of CD3+__ | 70.42 | | |
| % of Lymph__ | 56.22 | | |
| Abs. Count | 1131.23 | | |
| Parameter | Mean | SD | CV |
| FSC__ | 315.48 | 84.62 | 26.82 |
| SSC__ | 119.20 | 44.61 | 37.42 |
| CD3 FITC__ | 461.59 | 40.36 | 8.74 |
| CD4 PE__ | 511.42 | 26.85 | 5.25 |
| CD45 PerCP__ | 518.11 | 20.59 | 3.97 |
|  | CD4− | | |
| Cluster Membership | 359 | | |
| % of CD3+__ | 29.33 | | |
| % of Lymph__ | 23.41 | | |
| Abs. Count | 471.12 | | |
| Parameter | Mean | SD | CV |
| FSC__ | 334.63 | 84.84 | 25.35 |
| SSC__ | 142.16 | 44.20 | 31.09 |
| CD3 FITC__ | 434.55 | 37.67 | 8.66 |
| CD4 PE__ | 151.41 | 40.84 | 26.97 |
| CD45 PerCP__ | 510.85 | 22.82 | 4.46 |
|  | CD3− | | |
| Cluster Membership | 309 | | |
| % of Lymph__ | 20.15 | | |
| Abs. Count | 405.51 | | |
| Parameter | Mean | SD | CV |
| FSC__ | 360.95 | 92.12 | 25.52 |
| SSC__ | 150.00 | 49.70 | 33.13 |
| CD3 FITC__ | 122.42 | 50.06 | 40.89 |
| CD4 PE__ | 44.55 | 33.19 | 74.49 |
| CD45 PerCP__ | 484.68 | 22.81 | 4.70 |

There are several key differences between this report and one emanating from a "flat" classifier only capable of M mutually-exclusive populations.

First, a full set of population statistics is drawn on each population, regardless of its level in the hierarchy. Complex populations (LYMPHS, CD3$^+$ LYMPHS) have their own statistics summarizing all events that classified at these levels. In a "flat" classifier, these complex populations would not be reported on directly, but rather would require post-processing summation of underlying subsets.

Second, complex populations (i.e., those having subsets) have 2nd-order statistics (Standard Deviation and Coefficient of Variation). A "flat" classifier cannot form these statistics. Nor can they be post-processed by combining the 2nd-order statistics of component (leaf) subsets.

Third, for each population, a set of percentages is automatically computed which relates that population to all its "ancestor" supersets. This alleviates the analyst from having to post-process these percentages manually, as would be required using a "flat" classifier.

The absolute counts are obtained by a method already patented by Haynes and Shoor.

Hierarchical Attractor Engine has been reduced to practice in the medical diagnostic field of flow cytometry, however, its applicability to process control, scientific analysis, database processing, and information retrieval should be readily apparent to any skilled practitioner having a need for algorithmic cluster analysis. Flow cytometry is a general method for quantitative analysis of cell populations whereby multi-sensor photometric measurements are collected from cells stained with antigen-specific fluorochrome markers, whereby a stream of multi-parameter events is analyzed to classify and count cell populations for medical interpretation. The emerging art of highly-autonomous instrumentation capable of low-cost, high-reliability, clinical-throughput assays of biological cells and sub-cellular particles motivates the invention. In comparison to a skilled human analyst experienced at hand-clustering flow cytometry data, an autoclustering algorithm must arrive at the same numerical results to within 1 or 2 percent on good data, closely parallel the analyst's judgment in rejecting bad data (and otherwise assure the quality of reported output), assure quantitative and qualitative repeatability, and perform at considerably higher throughput than the human analyst.

It is apparent that many modifications and variations of this invention as herein set forth may be made without departing from the spirit and scope hereof. The specific embodiments described are given by way of example only and the invention is limited only by the terms of the appended claims.

DETAILED DESCRIPTION OF THE HIERARCHICAL ATTRACTOR ALGORITHM

The hierarchical attractor algorithm classifies an incoming stream or recorded list of multi-parameter events into a set of color-population scatterplots and a population statistics report. From the user's point of view, classification proceeds as a single, high-level operation applied to each specimen datafile. From the software engineer's point of view, the attractors algorithm is a two-stroke engine—it can be broken down into two sequential steps:

Pre-analysis Attractors adapt their positions to a subsequence of events

Classification—Attractors lock down in place and classify each event, then summarize population statistics Pre-analysis Algorithm (Recursive)

The following pseudo-code describes in detail the Pre-analysis algorithm whose job is to allow attractors to find their respective data centers-of-mass interacting against the current event vector stream or recording:

```
for (AllEventVectors)
```

```
    for (AllTopLevelAttrs)  // let each top level attr try to interact
    {
        if (theAttr->fInteracting)
            theAttr->PreAnalyzeEvent (EventVector);
    }
// do final update on each adaptive attr
for (AllAttrs&Sub-attrs)
    {
        if (!theAttr->fLockedDown)
        {
            theAttr->DataAdjustMidPointLocation();
            theAttr->fInteracting = FALSE;
            theAttr->fLockedDown = TRUE;
        } // for each attractor & sub-attractor
    }
```

The following pseudo-code describes in detail the function TAttrObject::PreAnalyzeEvent which is called repetitively in the above doubly-nested loop.

```
TAttrObject::PreAnalyzeEvent (Vector& Event)
{
if ( InsideAttractionBoundary(Event) )
    {
        fVectorSum.sigma_plus (Event);
        fInteractionCount++;
        if (fInteractionCount == fThresholdOfInertia)
        {
            fLockedDown = FALSE;
            this->DataAdjustMidPointLocation();
        }
        if ((fInteractionCount == fUpdateSchedule[0])  ||
            (fInteractionCount == fUpdateSchedule[1])  ||
            (fInteractionCount == fUpdateSchedule[2])  ||
            (fInteractionCount == fInteractionQuota))
                this->DataAdjustMidPointLocation();
        if (fInteractionCount == fInteractionQuota)
        {
            fInteracting = FALSE;
            fLockedDown = TRUE;
        }
        // now recurse at next lower level
        for (AllChildSubAttrs)  //let each next level sub-attr try to interact
        {
            if (ChildSubAttr->fInteracting)
                ChildSubAttr->PreAnalyzeEvent (Event);
        }
    } // if insideAttractionBoundary
}
```

The predicate used to compute InsideAttractionBoundary is the one described for "A Cigar-Shaped (Non-Spherical) Attractor Geometry" in (1). A scalar AttractionRadius, different from the one used for the classification boundary (MembershipRadius), governs how distant an event can fall from the attractor's centerline and still pull on it. This AttractionRadius is mouse-adjusted by the user.

The logic of the recursive pre analysis algorithm demands that an event fall within all of a population's "ancestor" attraction boundaries before being considered for "pulling" on a sub-attractor. This logic permits the sub-attractor to ignore all events in the data distribution which fall outside the compartment of which it is a subset.

Classification Algorithm (Recursive)

The following pseudo-code describes in detail the Classification algorithm whose job (after pre-analysis has completed) is to place every event vector into the population hierarchy:

```
for (AllEventVectors)
    {
        Boolean EventTakenByTopLevelAttr = FALSE;
        for(AllTopLevelAttrsinOrderOfClassificationPrecedence)
```

```
//let each top-level attr have a shot at the event
{
        TopLevelAttr->DoClassify(EventVector,
EventTakenByTopLevelAttr);
```

The following pseudo-code describes in detail the function TAttrObject::DoClassif which is called repetitively in the above doubly-nested loop.

```
TAttrObject::DoClassify(Vector& EventVec, Boolean&
EventAlreadyTakenAtMyLevel)
{
Boolean MemberOfThisAttractor = insideMembBound && !
EventAlreadyTakenAtMyLevel;
Boolean OrbiterOfThisAttractor = insideOrbBound && !
insideMembBound;
if (OrbiterOfThisAttractor) fOrbiterCount++;
Boolean EventTakenBySubAttr = false;
if (MemberOfThisAttractor)
    {
    // RECURSION HERE
    EventTakenBySubAttr = false;
    for (AllChildSubAttrsInOrderOfClassificationPrecedence)
        //let sub-attrs at the next event have a shot
        {
        theSubAttr->DoClassify(EventVec, EventTakenBySubAttr);
        }
    }
if (MemberOfThisAttractor)
    {
    EventAlreadyTakenAtMyLevel = TRUE; // inhibits lower precedence
attrs at              // same level from claiming
this event
        fMembershipCount++;
        fMembVectorSum.sigma_plus(EventVec);    //keep running
vector sum
        fMembVectorSumSq.sigma_plus_sq(EventVec); //keep running
sum-of-squares
        EventsClassTableEntry |= gClassBitMask[fClusterCode];
                // to support plot graphics
    }
}
```

The predicates used to compute insideMembBound and insideOrbBound are those described for "A Cigar-Shaped (Non-Spherical) Attractor Geometry" in (1).

The logic of the recursive DoClassify algorithm demands that an event fall within all of a population's "ancestor" membership boundaries before being considered for membership in a sub-attractor. This logic permits a sub-attractor to ignore all events in the data distribution which fall outside the compartment of which it is a subset.

Classification precedence resolves the competition to classify the same event among the set of top-level attractors (assuming the event satisfies more than one attractor's membership boundary). The attractor having the higher precedence classifies the event. Similarly, among the sibling sub-attractors descending from the same parent node, classification precedence resolves the competition to classify the event. Classification precedence is stored implicitly in the list order of sub-attractors, the user having the ability to rearrange precedence order by shuffling the list.

It is apparent that many modifications and variations of this invention as herein set forth may be made without departing from the spirit and scope hereof. The specific embodiments described are given by way of example only and the invention is limited only by the terms of the appended claims.

What is claimed is:

1. A method for classifying a sample of particles into one or more hierarchical clusters wherein multi-parameter data are collected for each particle within said sample, comprising the steps of:
   (a) collecting a plurality of parameters for each particle in a sample of particles;
   (b) displaying said parameters for each particle in the sample of particles on a set of two-dimensional scatterplots;
   (c) manually positioning a plurality of geometric boundary surfaces on the set of two-dimensional scatterplots for a plurality of top level clusters of particles so as to enclose a group of the displayed particles in each top level cluster, each geometric boundary surface having a user-defined, center location, shape, size, radius and orientation;
   (d) defining a vector for each particle in the sample of particles and testing if each vector is contained within each geometric boundary surface;
   (e) summing each vector contained within each geometric boundary surface to calculate a vector mean;
   (f) after a user-defined number of vectors are summed to calculate the vector mean, calculating a new center location for each geometric boundary surface using the vector mean;
   (g) moving each geometric boundary surface on the set of two-dimensional scatterplots to relocate the geometric boundary surface about the new center location;
   (h) repeating steps (d)–(g) until a user-defined number of vectors or all available vectors have been included in the calculation of a final center location;
   (i) moving each geometric boundary surface on the set of two-dimensional scatterplots to relocate the geometric boundary surface about the final center location;
   (j) comparing all subsequently received particles with each geometric boundary surface for inclusion within or exclusion outside the top level clusters associated with each geometric boundary surface;
   (k) selecting a plurality of mutually exclusive subclusters which comprise elements falling within one of the top level clusters of step (c) and defining the mutually exclusive sub-clusters as new top level clusters; and
   (l) repeating steps (c)–(k) until a desired number of cluster levels are achieved.

2. The method of claim 1 wherein each geometric boundary includes an orbital band set in step (c) for each cluster.

3. The method of claim 1 wherein orbital bands are set in step (ii) for one or more of the clusters.

4. The method of claim 1 wherein the particles comprise cells.

5. The method of claim 4 wherein the cells are labeled with at least one fluorescent marker prior to step (a) wherein each marker has an emission wavelength that is distinguishable from the other.

6. A method for classifying a sample of blood cells in a sample of such cells into two or more hierarchical clusters wherein multi-parameter data are collected for each of said cells, by means of flow cytometry, comprising the steps of:
   (a) manually positioning a geometric boundary surface on a series of two dimensional surfaces in the region where at least one cluster is expected, said boundary which will enclose a group of the cells displayed as a series of scatterplots on the two dimensional surfaces, so as to define a top level cluster with the geometric boundary surface having a user defined center location shape, size, radius, and orientation;
   (b) analyzing the cells by means of flow cytometry wherein at least two parameters of data are recorded for each cell analyzed;

(c) displaying said parameters for each blood cell in the sample of blood cells on said scatterplots;

(d) defining a vector for each cell analyzed and testing if each vector is contained within the geometric boundary surface;

(e) summing each vector contained within the geometric boundary surface to calculate a vector mean;

(f) after a user-defined number of vectors are summed to calculate the vector mean, calculating a new center location for the geometric boundary surface using vector mean;

(g) moving the geometric boundary surface on the set of two-dimensional scatterplots to relocate the geometric boundary surface about the new center location;

(h) repeating steps (d)–(g) until a user defined number of vectors or all available vectors have been included in the calculation of a final center location;

(i) moving the geometric boundary surface on the set of two dimensional scatterplots to relocate the surface about the final center location;

(j) comparing all subsequently received blood cells with the boundary surface for inclusion within or exclusion outside the top level cluster associated with the geometric boundary surface;

(k) selecting a plurality of mutually exclusive sub-clusters which comprise elements falling within one of the top level clusters of step (a) and defining the mutually exclusive sub-clusters as new top level clusters; and (l) repeating steps (a)–(k) until a desired number of cluster levels are achieved.

7. The method of claim 6 wherein the cells comprise leucocytes.

8. The method of claim 6 wherein the cells comprise lymphocytes.

9. The method of claim 8, wherein the clusters comprise lymphoyctes, $CD3^+$, $CD3^-$, $CD4^+$ and $CD4^-$ cells.

10. The method of claim 6 wherein the cells are labeled with at least one markers prior to step (i), wherein each marker has an emission wavelength that is distinguishable from the others.

11. The method of claim 6 wherein the cells in the sample have been labeled with immunofluorescent markers.

12. The method of claim 6 wherein the number of clusters levels is at least three.

13. The method of claim 6 wherein orbital bands are set for each cluster.

* * * * *